United States Patent [19]

Bartz

[11] 4,335,622
[45] Jun. 22, 1982

[54] SOIL GAS PROBE
[75] Inventor: Gerald L. Bartz, Amarillo, Tex.
[73] Assignee: Phillips Petroleum Company, Bartlesville, Okla.
[21] Appl. No.: 180,254
[22] Filed: Aug. 22, 1980
[51] Int. Cl.³ .............................................. G01N 1/24
[52] U.S. Cl. ................................ 73/864.74; 173/126; 173/129; 175/21; 175/135
[58] Field of Search ................. 73/864.74; 175/19, 21, 175/135; 173/90, 91, 126, 129, 30

[56] References Cited
U.S. PATENT DOCUMENTS

| | | | |
|---|---|---|---|
| 216,042 | 6/1879 | Le Grand et al. | |
| 1,845,709 | 2/1932 | Haddon | |
| 3,050,095 | 8/1962 | Prather | 144/193 |
| 3,084,553 | 4/1963 | Cullinan et al. | 73/421.5 |
| 3,087,560 | 4/1963 | Dodson | 175/314 |
| 3,198,265 | 8/1965 | Voelkerding | 173/74 |
| 3,307,912 | 3/1967 | Davis | 23/232 |
| 3,313,356 | 4/1967 | Clevenger | 173/91 |
| 3,490,288 | 1/1970 | Patnode | 73/421.5 |
| 3,835,710 | 9/1974 | Pogorski | 73/421.5 R |
| 4,261,203 | 4/1981 | Snyder | 73/864.74 |
| 4,310,057 | 1/1982 | Brame | 175/21 |

OTHER PUBLICATIONS

Helium Sniffer, Model 100, drawing by Phillips Petroleum Company, No. 7325.
Copending Application Ser. No. 12,786, now allowed, by Vona L. Snyder, now Pat. No. 4,216,203.

Primary Examiner—S. Clement Swisher

[57] ABSTRACT

Provided is a soil gas sampling probe having shaft extensions, a removable hammer and anvil combination to drive the shaft into the ground, a pointed rotation resistant probe tip, and a movable septum holder.

17 Claims, 7 Drawing Figures

SOIL GAS PROBE

BACKGROUND OF THE INVENTION

This invention relates to an apparatus for sampling soil gases, for example, an anomolous concentration of helium or other gases, which may be indicative of nearby hydrocarbon deposits, a geothermal reservoir, or deposits of radioactive ores.

Most rapid surveys which collect subsurface gaseous emanations use a probe that collects samples at a depth from about 18" to about 36" below ground surface. A shaft is driven to the desired depth, and a gas sample is taken through an aperture near the lower end of the shaft. At this depth the gas sample is a mixture of subsurface gases rising from the resource, biogenically produced gases, and air penetrating down from the surface. Dilution of the subsurface gas with air from the surface is undesirable, as it both dilutes gas concentrations and introduces foreign gases into the sample. Contamination of the sample by surface air can be minimized by driving a shaft into the earth, the dimensions of the shaft being such that it fills the cavity made as it is driven into the earth. A gas seal formed by the exterior wall of the shaft and the surrounding earth mitigates contamination of the sample by atmospheric air. Dilution of the sample by surface air can be further minimized by collecting the samples of gas at a depth of greater than about 6 feet.

Obstacles, such as packed gravel and large rocks, are frequently encountered as the shaft is sunk into the earth. As the probability of encountering such obstacles increases with the increasing depth to which the shaft is sunk, an apparatus for taking subsurface gas samples at for example a depth of 10 feet must be durable, easily repaired, and have good penetrating abilities.

Soil gas helium concentration is commonly only a few parts per million. Because helium is soluble in water, a helium sample taken from a high moisture content site can yield misleading results. It is thus important a gas probe have the capability of obtaining a soil sample and reliably transporting the same to surface for a moisture analysis.

OBJECTS OF THE INVENTION

It is thus an object of the present invention to provide a soil gas probe characterized by good penetrating abilities.

It is another object of this invention to provide a tip for a soil gas probe which is characterized by a high resistance to rotation.

It is another object of this invention to provide a tip for a soil gas probe having the capability to reliably transport a sample of subsurface soil to the surface.

It is another object of this invention to provide a soil gas probe having the capability of taking a subsurface gas sample of the depth of greater than about 6 feet.

It is another object of this invention to provide a soil gas probe which is easily repaired.

SUMMARY OF THE INVENTION

According to one aspect of the present invention, a tip for a soil gas probe is provided with a generally cylindrical portion adjacent its upper end, a penetrating portion converging from the generally cylindrical portion to the lower end, and at least one elongated generally longitudinally extending recess in the surface of the converging portion. As the tip is driven into the earth, soil is packed into the elongated recess and provides the tip with high resistance to rotation, which simplifies exposing a sampling port near the lower end of the probe. The generally cylindrical upper portion of the tip creates a well defined cavity in the earth which is readily sealed by the shaft of the probe.

According to another aspect of the present invention, a shaft for a soil gas probe is provided comprising an elongated tubular member having a male fitting at one end and a complementary female fitting at the other end and at least one pair of recessed opposed flat portion on the exterior surface intermediate its upper end and its lower end. A collar can be attached to the shaft at the position provided with the recessed flats and the shaft driven into the earth by hammer blows against the collar. Another shaft, which can be identical, can then be fitted to the end of the shaft protruding from the earth, the collar from the first shaft removed and placed on the recessed flats on the second shaft and the process continued until the shaft is sunk to the desired depth.

According to another aspect of the present invention, a collar providing a hammering surface on a soil gas probe is adapted for being removably fitted to a pair of recessed opposed flats on a cylindrical shaft.

According to another aspect of the present invention, an upper gas seal for a soil gas probe is provided comprising a septum, a capillary tube, a septum holder having a passage therethrough defined at one end by the capillary tube and closed at the other end by the septum, and means for slidably mounting the septum holder to the soil gas probe. The gas seal is especially adapted to be employed with a soil gas probe utilizing a capillary hose for conveying the gas sample from the lower end of the probe to the upper end and having an extendable shaft.

These and other features of the present invention will be made more apparent from the following detailed description of the invention, the drawings, and the attached claims.

DETAILED DESCRIPTION OF THE INVENTION

Figure 1:
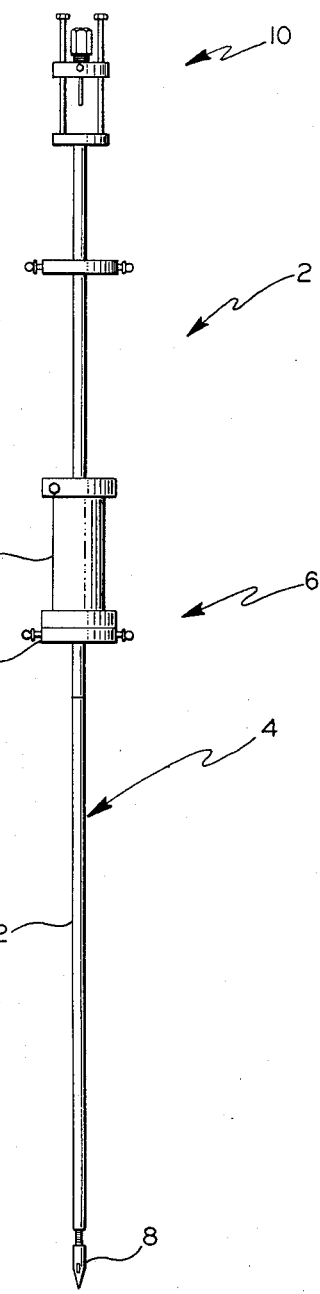
FIG. 1 is an elevational view illustrating certain features of the present invention.
Figure 2:
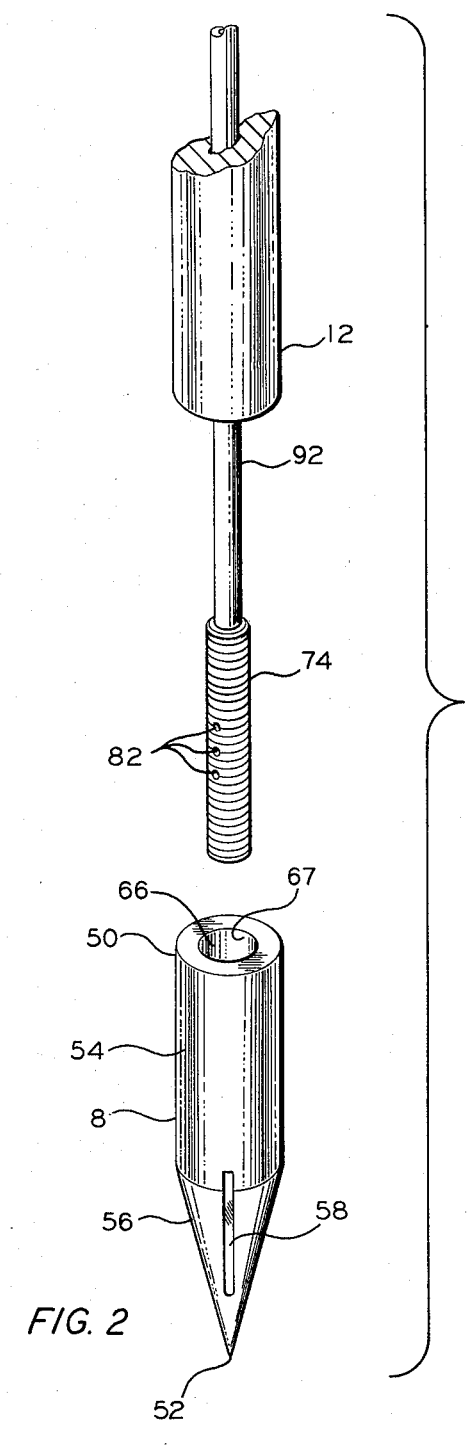
FIG. 2 is a detailed fragmented perspective exploded view of a portion of the apparatus of FIG. 1.

Referring to FIG. 1, a gas probe, designated generally by the reference numeral 2, comprises a shaft 4, a driving assembly designated generally by the reference numeral 6 cooperating with the shaft 4, a tip 8, and means for conveying subsurface gases from adjacent the tip 8 to a sealing assembly designated generally by the reference numeral 10 at the upper end of the shaft 4.

Figure 3:
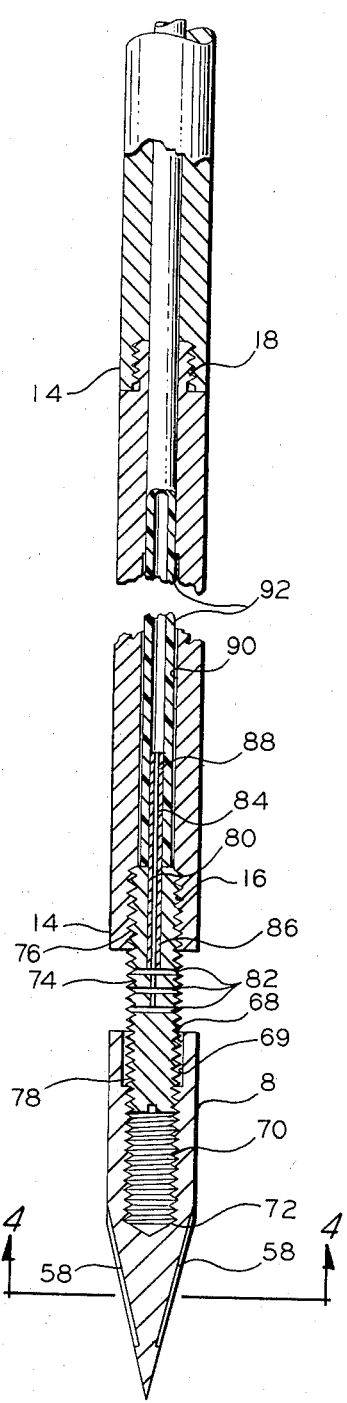
FIG. 3 is a detailed fragmented longitudinal cross sectional view of a portion of the apparatus of FIG. 1.
Figure 7:
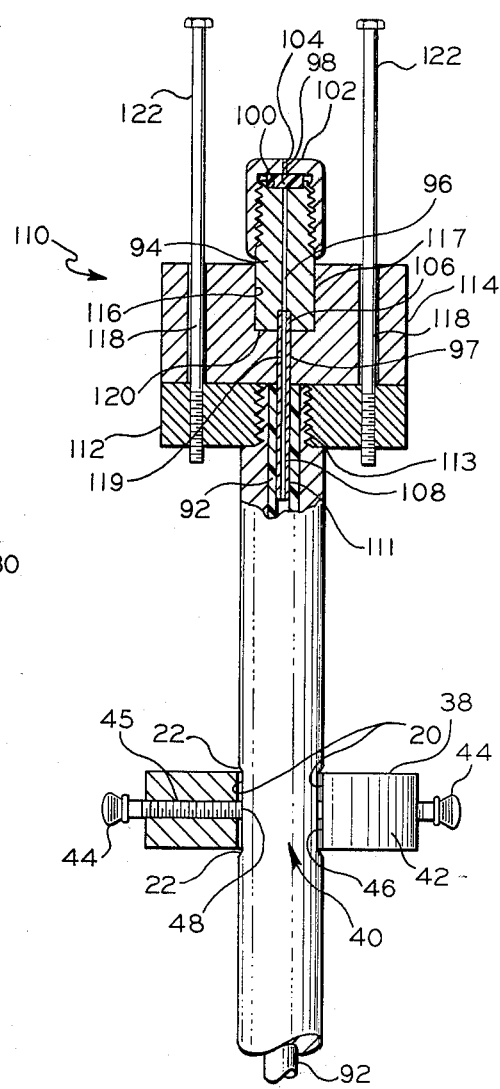
FIG. 7 is a detailed fragmented longitudinal cross sectional view of a portion of the apparatus of FIG. 1.

The shaft 4 is constructed from at least one elongated tubular member 12. Each tubular member 12 has a longitudinal axis and is preferably generally cylindrical in shape having a uniform outside diameter from top to bottom. As best shown in FIG. 3, each of the tubular members 12 is provided with a pair of complementary fittings 14 on each of its ends. Preferably, the tubular member 12 is provided with a female threaded fitting 16 on its lower end and a male threaded fitting 18 on its upper end. In this manner, any desired number of tubular members 12 can be axially linked together to form the shaft 4. As shown in FIG. 7, each generally tubular member 12 is provided with at least one pair of opposed flats 20 intermediate its ends. Preferably, each of the flats 20 is recessed so as not to cause interference with the gas seal between the shaft 4 and the surrounding earth. In this embodiment, each flat 20 is bounded at its upper and lower ends by a longitudinally facing shoulder 22, the pair of flats 20 forming a pair of shoulders 22 at a longitudinal position on the tubular member 12. Preferably, the shoulder 22 is generally segmental in shape. Preferably, according to the invention, each tubular member 12 is provided with three pairs of opposed flats 20 spaced, for example, about 18 inches apart. Each tubular member 12 can conveniently be, for example, about 4 feet in length and have an outside diameter for example of between about ⅜ of an inch and ⅝ of an inch. The flats 20 are conveniently milled into the exterior surface of the tubular member 12. For convenience, each flat 20 can have a maximum depth of, for example, about 1/16 of an inch and a longitudinal length of about ¾ of an inch.

Figure 6:
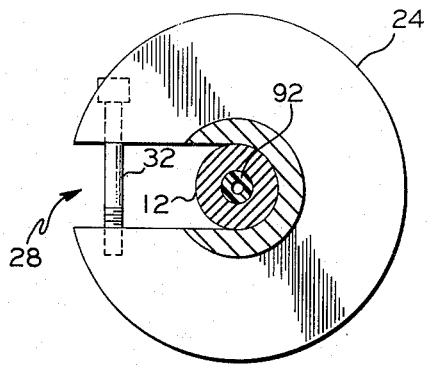
FIG. 6 is a cross sectional view of a portion of the apparatus as seen in FIG. 5 taken along the lines 6—6.
Figure 5:
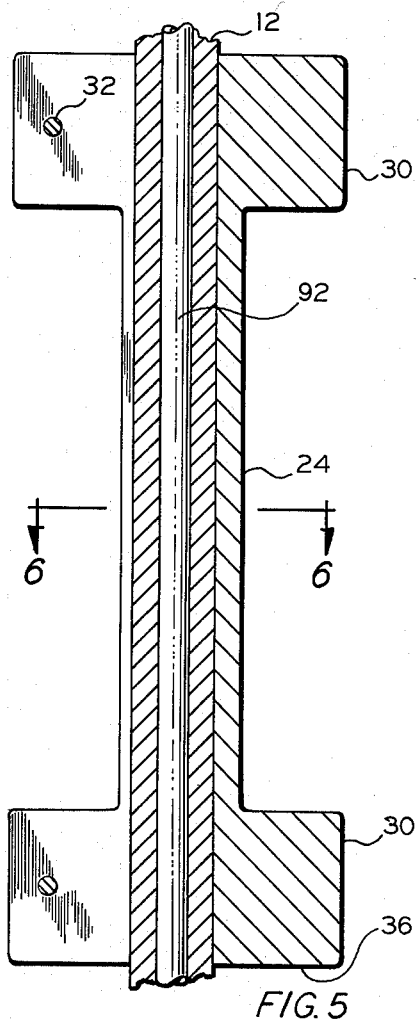
FIG. 5 is a partial fragmented longitudinal cross sectional view of a portion of the apparatus of FIG. 1.

The driving assembly 6 comprises a mass 24 slidably mounted on the shaft 4 and a mass 26 fixedly mounted on the shaft 4. Preferably, the mass 24 comprises a slidable hammer mounted to the shaft 4. As shown in FIG. 5 and 6, the hammer 24 is elongated and provided with a longitudinally extending slot 28 extending radially inward from its exterior surface and encompassing its longitudinal axis, as best shown in FIG. 6. The hammer 24 is slidably mounted to the shaft 4 by slot 28, which has a width and depth sufficient to receive the shaft 4 along the longitudinal axis of the hammer 24. Preferably, the hammer 24 is provided with an enlarged portion 30 at each of its ends. A removable set screw 32 can be mounted across the slot 28 to retain the hammer 24 on the shaft 4. Preferably, the set screw 32 traverses the slot 28 through the enlarged end portion 30 of the hammer 24. The hammer 24 is provided with a generally planar surface 36 on at least one of its ends and has a sufficient mass to enable the shaft 4 to be easily driven to the desired depth, for example the weight of about 8–10 pounds. The hammer 24 can be constructed preferably in one piece of any suitable material, for example, stainless steel.

The planar surface 36 of the hammer 24 is in juxtaposed relationship with a generally planar hammering surface 38 of the mass 26. The surface 38 provides a hammering surface for striking by planar surface 36 of the hammer 24. The mass 26 functions to transfer the energy of the falling hammer to the shaft 4 and drives it into the earth. The mass 26 preferably is in the form of a collar which is affixed to the shaft 4 at the pair of opposed flats 20. The collar 26 is provided with a slot 40 which extends radially inward from a side surface 42 of the collar 26 and encompasses the longitudinal axis of the collar 26. The slot 40 is perpendicular to the planar surface 38 of the collar 26. The collar 26 is mounted on the shaft 4 at a position so that an inside wall 46 of the slot 40 closely opposes a flat 20. Preferably, a portion of the collar 26 abuts against the shoulder 22 of the shaft 4. Preferably, the slot 40 is of sufficient width and depth to receive the shaft 4 so that the longitudinal axis of the collar 26 coincides with the longitudinal axis of the shaft 4. A set screw 44 is mounted in a passage 45 generally parallel to the planar surface 38 of the collar 26 and extends perpendicularly from the inside wall 46 of the slot 40 to the side surface 42 of the collar 26. A bottom end 48 of the set screw 44 engages the flat 20 and extends along a radius from the longitudinal axis of collar 26. The set screw 44 aids in retaining the collar 26 on the shaft 4 as the shaft is driven into the earth by the impact of the hammer surface 36 against the collar surface 38. Preferably, the collar 26 is generally disc shaped, having a diameter of at least twice its length and is provided with a generally radially disposed slot.

Figure 4:
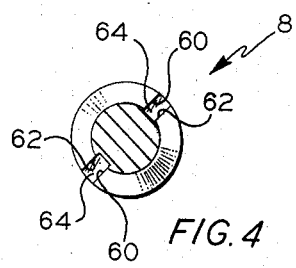
FIG. 4 is a cross sectional view of a portion of the apparatus of FIG. 3 taken along the lines 4—4.

The tip 8 is provided with an upper end 50, a lower end 52, preferably a point, a generally cylindrical surface portion 54 extending from the upper end 50 and a penetrating portion 56 converging from the generally cylindrical surface portion 54 to the point 52. The cylindrical surface portion 54 of the tip 8 has a diameter no greater than the diameter of the shaft 4. Preferably, the shaft 4 and cylindrical surface portion 54 of the tip 8 have the same diameter. The penetrating portion 56 of the tip 8 can diverge from the point at any suitable angle, for example, an angle of between about 25° and 35°. A diverging angle of about 28° has been used with good results. The penetrating portion 56 of the tip 8 is further provided with at least one elongated generally longitudinally extending recess 58 in its surface. The recess 58 provides the tip with rotation resistance when the tip 8 is driven into the earth. Preferably, the penetrating portion 56 is generally conical in shape and the longitudinally extending recess 58 defines a channel having a pair of generally planar side surfaces 60 and 62 and a generally planar bottom surface 64 which is disposed radially inward from the conical surface of the penetrating portion 56 of the tip 8 as best seen in FIG. 4. Preferably, the channel 58 opens onto the generally cylindrical surface portion 54 of the tip 8. In this embodiment, the bottom surface 64 of the channel 58 forms an elongated recessed ramp extending between the penetrating portion 56 and the cylindrical portion 54 of the tip 8. Preferably, the tip is provided with an opposed pair of channels 58, as such an arrangement has been employed with good results. The channels 58 can be of any suitable dimension. For example, for a tip having a maximum diameter of ⅝ inches, each channel can have a maximum depth of 1/32", a width of 1/16", and a length of ½ inch, beginning, for example, 5/16 inches from the point. The tip 8 is further provided with an axial bore 66 defined by a generally cylindrical interior surface 67 extending from the upper end 50 of the tip 8. Bore 66 is provided with an untapped portion 69 adjacent its upper end to partially define tubular chamber 68 adjacent the upper end of the tip 8 when the tip is mounted adjacent the lower end of the shaft 12. The bore 66 is also provided with a threaded portion 70 adjacent its lower end 72. Preferably, the lower end of the bore 66 is provided with counterclockwise threads for a purpose which will be hereinafter described.

The apparatus 2 is provided with means for conveying gases from adjacent its lower end to its upper end. A connector 74 is threadably affixed to the lower end of the shaft 4. The connector 74 has a generally cylindrical upper threaded exterior surface 76 and a generally cylindrical lower threaded exterior surface 78. The tubular chamber 68 is defined between the untapped portion 69 of the interior surface 67 of the tip 8 and the connector 74. Preferably, the lower threaded surface 78 of the connector is provided with counterclockwise threads for engagement with a counterclockwise threaded portion 70 of the tip 8. The upper threaded surface 76 of the connector 74 is engaged with the female threaded fitting 16 of the tubular member 12. The connector 74 has an axial passage 80 extending through its upper threaded portion 76. The axial passage 80 communicates with at least one transverse passage 82 communicating to form a sample inlet port in the side of the connector 74 preferably intermediate the upper threaded surface 76 and the lower threaded surface 78. A capillary tube 84 has a lower portion 86 mounted sealingly within the axial passage 80 of the connector 74 and an upper portion 88 extending axially away from the passage 80 and into a passage 90 extending axially through the tubular member 12. The passage through the capillary tube forms a flow passage from the outside of the connector 74 into a capillary hose 92. The capillary hose 92 is mounted sealingly over the upper portion 88 of the capillary tube 84 and extends within the passage 90 through the tubular member 12 to the upper end of the shaft 4. Preferably, the capillary hose 92 has an inside diameter of less than about 1 millimeter to minimize dead air space and is constructed of silicon rubber, which resists helium penetration and is heat resistant.

The sealing assembly 10 is mounted at the upper end of the shaft 4. The sealing assembly 10 comprises a septum holder 94, which is preferably generally cylindrical in shape and has an axial passage 96 extending therethrough. A septum 98 seals one end of the passage 96. Preferably, the septum 98 is made of a helium impermeable material such as silicon rubber, has a disc-like shape and is seated in a recess 100 in the upper end of the septum holder 94. A drawdown nut 102 having an inside flange at one end with an axial passage 104 therethrough is provided at the upper end of the septum holder 94 to compress the septum 98 and reliably seal the end of the passage 96. A capillary tube 108 has an upper portion 106 sealingly mounted in the axial passage 97 of the septum holder 94 and a lower portion 11 extending axially from the septum holder 94 and forming an elongation of the passage 96. The lower portion 111 of the capillary tube 108 is mounted sealingly within the upper end of the capillary hose 92. A flow passage is thus provided extending from the aperture 82 to the septum 98 longitudinally through the apparatus 2.

The septum holder 94 is movably mounted to the end of the shaft 4 by means 110. As illustrated in FIG. 7, the means 110 comprises a block 112 affixed to the upper end of the shaft 4, preferably threadably affixed via a passage 113 through the block 112 as shown. Preferably, the block 112 has a generally annular shape. A second block 114 is movably mounted vertically adjacent the first block 112. Preferably, the second block 114 is movably mounted for longitudinal movement with respect to block 112 and the end of shaft 4. The second block 114 is provided with a primary passage 116 having a first diameter passage 117 and a second smaller diameter 119 and, as shown, a pair of secondary passages 118 parallel to the primary passage 116. The septum holder 94 is sealingly mounted at least partially within the large diameter primary passage 117. Preferably, the passage 117 is provided with a shoulder 120 for partially supporting the lower end of septum holder 94. The capillary tube 108 extends axially through the smaller diameter passage 119 of the second block 114. A pair of shafts 122 are rigidly mounted to the block 112 and extend in a direction which is parallel to the passage 113 away from the block 112 through the secondary passages 118 of block 114. The second block 114 is slidably mounted on shafts 122 for longitudinal movement with respect to the block 112 and the upper end of shaft 4. The capillary tube 108 is thus movable from a first position wherein the capillary tube 108 is positioned within the passage 113 to a second position in axial alignment with and spaced above the passage 113. Preferably, the shafts 122 each comprise an elongated bolt.

Operation of the apparatus 2 is as follows. A piece of capillary hose 92 is cut to approximately and preferably slightly greater than the desired sampling depth, for example, about 12 feet. A piece of wire, slightly longer than the tubular members 12 employed, for example, 4½ feet, is secured into one end of the capillary hose 92 and employed to pull the capillary hose 92 through the tubular member 12. The other end of the capillary hose 92 is then pressed over the capillary tube 80 extending from the connector 74 for mounting the tip 8 to the tubular member 12. The tubular member 12 is then threaded onto the connector 74, to mitigate twisting of the capillary hose. The tip 8 is then threaded counterclockwise onto the connector 74. The collar 26 is then mounted on the pair of flats 20 provided in the exterior surface of the tubular member 12. The set screws 44 are tightened. The hammer 24 is mounted on the tubular member 12 above the collar 26 and the retaining set screw 32 in the hammer 24 tightened, if desired. A collar 26 can be mounted if desired above the hammer 24 on another opposed pair of flats 20 provided on the tubular member 12 to prevent the hammer 24 from comming off the top of the shaft 4. The probe tip 8 is then placed over the location from which the soil gas sample is desired and the shaft 4 driven into the ground by hammer blows against the planar surface 38 of the collar 26. The collar(s) 26 are desirably moved upward stepwise on the opposed flats 20 as the shaft 4 is driven into the ground. The flexible capillary hose 92 is pulled through additional tubular members 12 which are affixed to the end of the tubular member 12 which protrudes from the ground as needed. After the desired number of tubular members 12 have been sunk into the earth, the sealing assembly 10 is affixed to the end of the shaft 4 and the capillary tube 108 protruding from the septum holder 94 is pressed into the upper end of the flexible capillary hose 92. The septum holder 94 can be moved as desired by the movably mounting means 110. After the capillary tube 108 is pressed into the capillary hose 92, the upper block 114 of means 110 can be lowered into contact with the lower block 112. The apparatus can be assembled before being driven into the earth if desired. The shaft 4 is then screwed away from the probe tip 8 to expose the sample ports 82 by clockwise rotation. The advantage of employing a counterclockwise thread in the tip 8 is that the shaft 4 can be screwed away from the tip 8 without the plurality of tubular members 12 becoming unscrewed from each other. The sample ports 82 in the side of the connector are exposed and a subsurface gas sample drawn up the capillary hose 92 and through the septum 98 at the upper end of the flow passage partially defined by the capillary hose 92 by any suitable means for piercing the septum and drawing a sample. The apparatus 2 can then be moved up and down slightly by hammer 24 blows if necessary to collect a soil sample in the tubular chamber 68 defined between the probe tip 8 and the connector 74. The shaft 4 is then screwed down into contact with the probe tip 8 to prevent contamination of the collected soil sample in the tubular chamber 68 as the apparatus 2 is withdrawn from the earth. It is advisable to remove the shaft 4 from the earth by reverse impact of the hammer 24 on a collar 26 located above the hammer, to avoid bending the shaft 4. The shaft 4 can be disassembled for ease in transportation. The gas sample withdrawn through the septum 98 is analyzed by any suitable means. The soil sample in the tubular chamber 68 of the tip 8 is analyzed for moisture content, for example.

Although the invention has been described in detail for purposes of explanation and illustration, it is not intended to be limited thereby. Rather, reasonable modifications and additions which would be apparent to one with ordinary skill in the art are included within the scope of this invention.

That which is claimed is:

1. A tip for a soil gas probe, said tip having an upper end, a lower end, and a longitudinal axis, with a generally cylindrical surface portion of the tip extending from the upper end of the tip toward the lower end of the tip and a penetrating portion of the tip converging from the generally cylindrical portion to a point at the lower end of the tip, the penetrating portion of the tip having at least one elongated generally longitudinally extending channel in its surface.

2. A tip as in claim 1 wherein the penetrating portion of the tip is generally conical in shape.

3. A tip as in claim 2 wherein the at least one elongated generally longitudinally extending recess defines a channel having a pair of generally planar side surfaces and a generally planar bottom surface.

4. A tip as in claim 3 wherein the channel opens onto the generally cylindrical surface portion of the tip.

5. A tip as in claim 4 wherein an axial bore extends partially through the tip from the upper end.

6. A tip as in claim 5 wherein the bore has an upper end and a lower end and is provided with a freebored portion adjacent its upper end and a counterclockwise threaded portion adjacent its lower end.

7. A tip as in claim 6 having an opposed pair of elongated channels.

8. A shaft for a soil gas probe comprising an elongated tubular member having an exterior surfacing of a uniform outside diameter, an upper end, a lower end, and a longitudinal axis with a female threaded connecting portion at its lower end a matching male threaded connecting portion at its upper end and at least one pair of recessed, opposed, flats on a portion of its exterior surface intermediate its upper end and its lower end.

9. A shaft as in claim 8 wherein the pair of recessed, opposed flats form a pair of longitudinally facing shoulders at a longitudinal position on the exterior surface of the shaft.

10. A shaft as in claim 8 wherein the shaft is provided with three pairs of recessed, opposed flats spaced apart along its exterior surface.

11. A hammering surface for a soil gas probe comprising:
(a) a mass having a longitudinal axis, a planar end surface perpendicular to the longitudinal axis, a side surface, and a longitudinally extending slot extending from the side surface and encompassing the longitudinal axis of the mass, said slot being perpendicular to the end surface of the mass; and
(b) at least one screw mounted in a passage extending partially through the mass from the side surface of the mass, the screw positioned on a radius from the longitudinal axis of the mass and being perpendicular to the slot.

12. A hammering surface as in claim 11 wherein the mass is generally disc-shaped.

13. An upper gas seal for a soil gas probe, said upper gas seal comprising:
(a) a first block having a passage therethrough and adapted to be mounted on the end of a shaft;
(b) a septum;
(c) a capillary tube;
(d) a septum holder having a passage therethrough with the septum sealing one end of the passage and the capillary tube extending axially from and forming an elongation to the passage at its other end;
(e) means for movably mounting the septum holder to the first block so that the capillary tube is movable from a first position with the capillary tube within the passage in the first block to a second position wherein the capillary tube is spaced above and in axial alignment with the passage in the first block.

14. A gas seal as in claim 13 wherein the means for slidably mounting the septum holder comprises:
(a) a second block having a primary passage and a pair of secondary passages therethrough, said secondary passages being parallel to the primary passage, with the septum holder being mounted at least partially within the primary passage; and
(b) a pair of shafts mounted to the first block and extending away from the first block in a direction which is parallel to the passage through the first block, wherein the pair of shafts extend slidably through the secondary passages in the second block.

15. A soil gas probe comprising:
(a) at least one tubular shaft having a uniform outside diameter a male threaded end and a female threaded end and a pair of recessed, opposed flats intermediate the male end and the female end;
(b) a capillary hose disposed within and extending for substantially the length of the tubular shaft;
(c) a connector having an exterior surface and affixed to one end of the capillary hose and the female threaded end of the shaft;
(d) a tip threadably affixed to the connector, said tip having an upper end and a lower end and having a generally cylindrical surface portion which extends from the upper end of the tip toward the lower end and has a diameter no greater than the outside diameter of the tubular shaft and a generally conical surface portion of the tip converging from the generally cylindrical surface portion to a point at the lower end of the tip, the conical surface portion of the tip being provided with at least one elongated generally longitudinally extending recess in its surface;
(e) a mass having a longitudinal axis, a planar end surface perpendicular to the longitudinal axis, a side surface, and a slot perpendicular to the planar end surface extending from the side surface and encompassing the longitudinal axis of the mass mounted to the shaft with the slot closely fitting the pair of recessed, opposed flats intermediate the male end and the female end of the shaft;

(f) an elongated mass having a longitudinal axis, a longitudinal slot encompassing the longitudinal axis, and a planar end surface perpendicular to the longitudinal axis slidably mounted on the shaft with the planar end surface of the elongated mass facing the planar end surface of the mass;

(g) a septum;

(h) a capillary tube inserted into the capillary hose at a location adjacent the male threaded end of the shaft;

(i) a septum holder having a passage therethrough with the septum sealing one end of the passage and the capillary tube extending axially from and forming an elongation to the passage at its other end;

(j) a first block having a passage therethrough threadably mounted by its passage to the male end of the shaft; and (k) means for slidably mounting the septum holder to the first block so that the capillary tube is movable from a first position where the capillary tube is within the passage in the first block to a second position wherein the capillary tube is spaced above and in axial alignment with the passage in the first block.

16. A gas probe as in claim 15 wherein the means for slidably mounting the septum holder comprises:

(a) a second block having a primary passage and a pair of secondary passages therethrough, said secondary passages being parallel to the primary passage, with the septum holder being mounted at least partially within the primary passage; and (b) a pair of shafts mounted to the first block and extending away from the first block in a direction which is parallel to the passage through the first block wherein the pair of shafts extend slidably through the secondary passages in the second block.

17. A gas probe as in claim 16 wherein the connector is provided with a flow passage extending between the exterior surface of the connector and the capillary hose.

* * * * *